US012667635B2

(12) United States Patent
Oguma et al.

(10) Patent No.: US 12,667,635 B2
(45) Date of Patent: Jun. 30, 2026

(54) ACTIVE OXYGEN SUPPLY APPARATUS

(71) Applicant: CANON KABUSHIKI KAISHA, Tokyo (JP)

(72) Inventors: Toru Oguma, Shizuoka (JP); Takumi Furukawa, Shizuoka (JP); Masaki Ozawa, Shizuoka (JP)

(73) Assignee: Canon Kabushiki Kaisha, Tokyo (JP)

( * ) Notice: Subject to any disclaimer, the term of this patent is extended or adjusted under 35 U.S.C. 154(b) by 754 days.

(21) Appl. No.: 18/186,336

(22) Filed: Mar. 20, 2023

(65) Prior Publication Data

US 2023/0226235 A1 Jul. 20, 2023

Related U.S. Application Data

(63) Continuation of application No. PCT/JP2021/040479, filed on Oct. 26, 2021.

(30) Foreign Application Priority Data

Oct. 29, 2020 (JP) ................................. 2020-181668

(51) Int. Cl.
$A61L\ 2/202$ (2026.01)
$A61L\ 2/10$ (2026.01)
$A61L\ 2/24$ (2006.01)

(52) U.S. Cl.
CPC .................. $A61L\ 2/202$ (2013.01); $A61L\ 2/10$ (2013.01); $A61L\ 2/24$ (2013.01)

(58) Field of Classification Search
None
See application file for complete search history.

(56) References Cited

U.S. PATENT DOCUMENTS

| | | | | |
|---|---|---|---|---|
| 7,214,412 B2 * | 5/2007 | Nishiguchi | ............ | G03G 9/091 |
| | | | | 438/763 |
| 2011/0212185 A1 | 9/2011 | Tanaka et al. | | |
| 2012/0111359 A1 * | 5/2012 | Mueller | .................. | A61L 2/202 |
| | | | | 134/1.1 |

FOREIGN PATENT DOCUMENTS

| | | | | | |
|---|---|---|---|---|---|
| JP | 62237733 A | * | 10/1978 | | |
| JP | 64-25865 A | | 1/1989 | | |
| JP | 2003209108 A | * | 7/2003 | ....... | H01L 21/02255 |
| JP | 4376496 B2 | * | 12/2009 | .............. | C23C 8/12 |
| JP | 2017-527521 A | | 9/2017 | | |
| KR | 20060006854 A | * | 1/2006 | ............. | H10D 1/716 |

(Continued)

OTHER PUBLICATIONS

International Search Report in International Application No. PCT/JP2021/040479 (Jan. 2022).

*Primary Examiner* — Andrew Smyth
(74) *Attorney, Agent, or Firm* — Venable LLP

(57) ABSTRACT

An active oxygen supply apparatus includes a casing, a plurality of plasma generating devices provided in an inside of the casing and configured to generate an induced flow containing ozone, an ultraviolet light source provided in the inside of the casing and configured to irradiate the induced flow containing the ozone with ultraviolet light, and a shielding plate provided in the inside of the casing and configured to shield the ultraviolet light irradiated to an outside of the casing through an opening portion of the casing. An active oxygen generated by irradiating the induced flow containing the ozone with the ultraviolet light from the ultraviolet light source supplies to the outside of the casing through the opening portion of the casing.

19 Claims, 12 Drawing Sheets

(56) References Cited

FOREIGN PATENT DOCUMENTS

| | | | |
|---|---|---|---|
| WO | 2010/032765 | A1 | 3/2010 |
| WO | 2016/012998 | A1 | 1/2016 |
| WO | 2022/092325 | A1 | 5/2022 |

* cited by examiner

ACTIVE OXYGEN SUPPLY APPARATUS

CROSS REFERENCE TO RELATED APPLICATIONS

This application is a continuation application of International Application No. PCT/JP2021/040479, filed Oct. 26, 2021, which claims the benefit of Japanese Patent Application 2020-181668, filed Oct. 29, 2020. Both prior applications are hereby incorporated by reference herein in their entirety.

TECHNICAL FIELD

This invention relates to an active oxygen supply apparatus.

BACKGROUND ART

Ultraviolet rays and ozone are known as means for sterilizing objects. In the conventional method of sterilization by ultraviolet rays, there was a problem that only a portion of a processed object that is irradiated by the ultraviolet rays is sterilized. In the Japanese Patent Application Laid-Open No. H01-25865, a sterilization device including an ozone supply apparatus, an ultraviolet rays generating lamp, and an agitator is used to generate an active oxygen by irradiating an ozone with ultraviolet rays from the ultraviolet rays generating lamp. The patent application discloses a method for sterilizing even shadow areas of the processed object that are not irradiated with ultraviolet rays by agitating the generated active oxygen.

SUMMARY OF THE INVENTION

However, in the sterilization apparatus disclosed in the Japanese Patent Application Laid-Open No. H01-25865, the processed object must be placed inside the sterilization apparatus, therefore, the sterilization apparatus has to become larger.

Problem to be Solved by the Invention

A purpose of the present invention of this patent application is, while keeping a sterilization apparatus which supplies an active oxygen from becoming larger depending on a size of a processed object, but to sterilize the processed object.

Means for Solving the Problem

To solve the aforementioned problems, the present invention includes the following configuration.

An active oxygen supply apparatus comprising:

a casing;

a plurality of plasma generating devices provided in an inside of the casing and configured to generate an induced flow containing ozone;

an ultraviolet light source provided in the inside of the casing and configured to irradiate the induced flow containing the ozone with ultraviolet light; and a shielding plate provided in the inside of the casing and configured to shield the ultraviolet light irradiated to an outside of the casing through an opening portion of the casing, wherein an active oxygen generated by irradiating the induced flow containing the ozone with the ultraviolet light from the ultraviolet light source is supplied to the outside of the casing through the opening portion of the casing.

EMBODIMENTS FOR CARRYING OUT THE INVENTION

Figure 1:
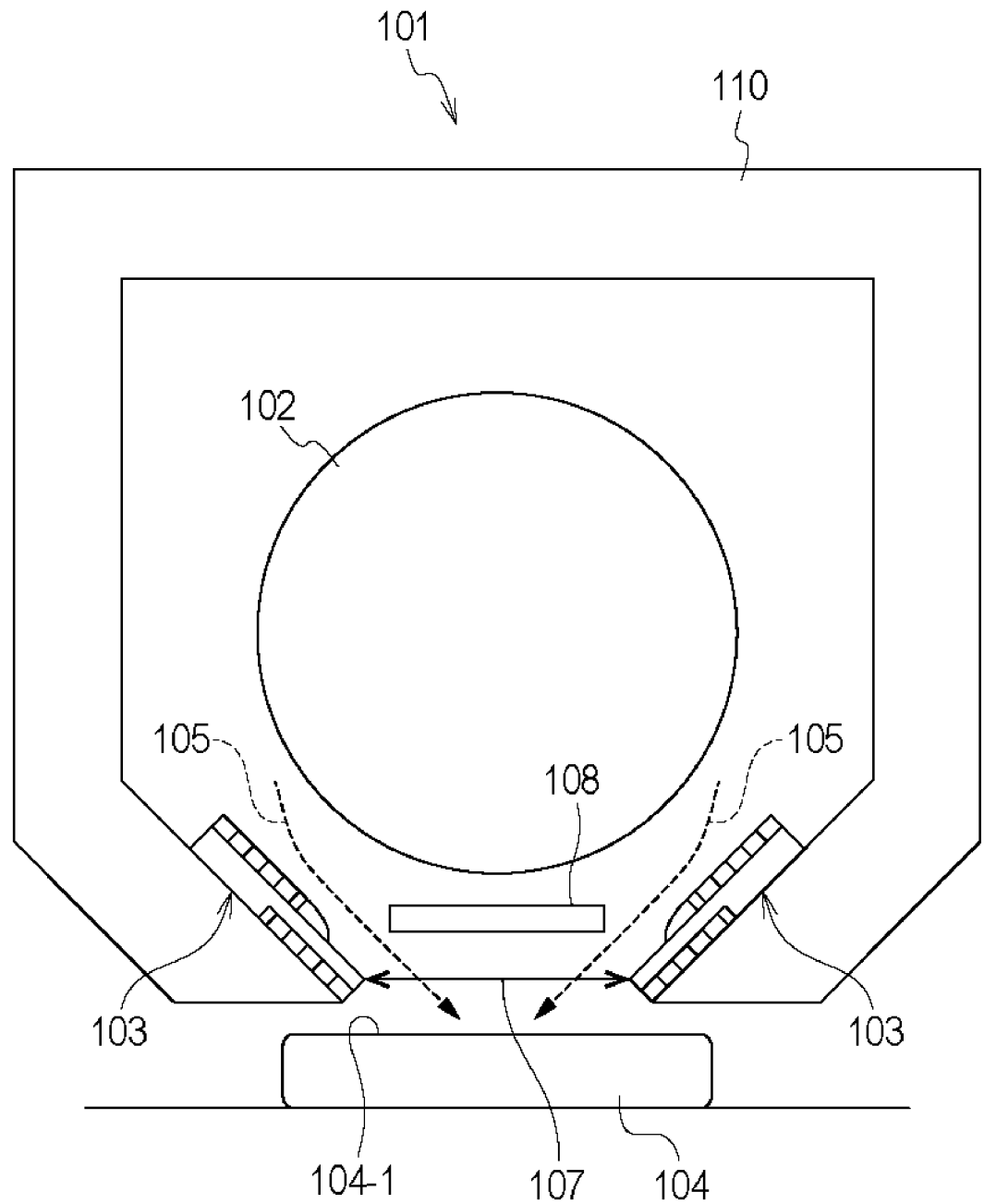
FIG. 1 is a cross-sectional view of an active oxygen supply apparatus 101 of an Embodiment 1.

In the following, a more detailed description of embodiments for carrying out the present invention is disclosed in accordance with the drawings. However, dimensions, materials, shapes, and relative dispositions of components described in the embodiments may be changed as appropriate depending on configurations of the components to which the present invention is applied and various other conditions. In other words, it is not intended to limit a scope of the present invention to the following embodiments.

In addition, in the present invention, statements of "equal to or more than XX and equal to or less than YY" or "from XX to YY" representing a numerical range means a numerical range including the lower and upper limits, which are end points, unless otherwise noted. When numerical ranges are described in stepwise, upper and lower limits of each numerical range can be arbitrarily combined.

In addition, in the following description, components that have the same function may be numbered identically in the drawings and their description may be omitted.

Embodiment 1

Figure 2A:
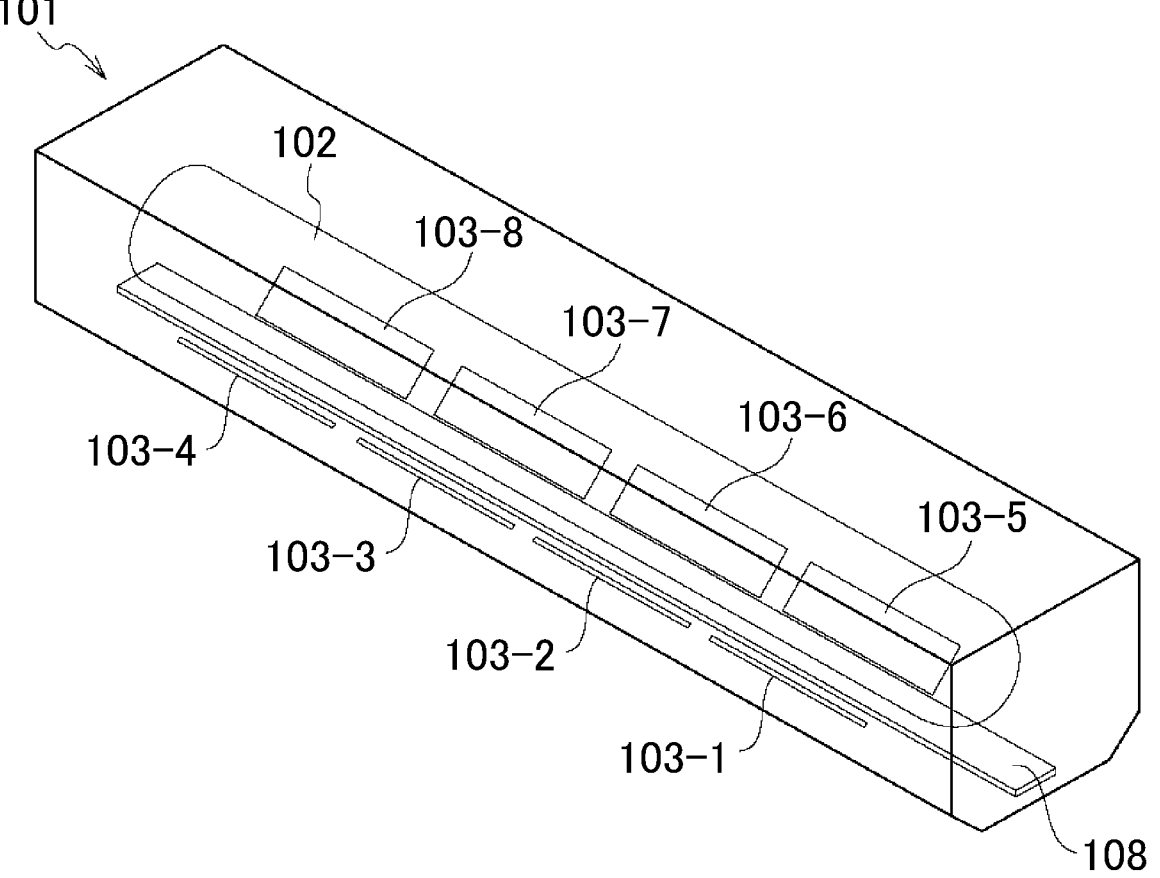
FIG. 2A is a perspective view of the active oxygen supply apparatus 101 of the Embodiment 1.
Figure 2B:
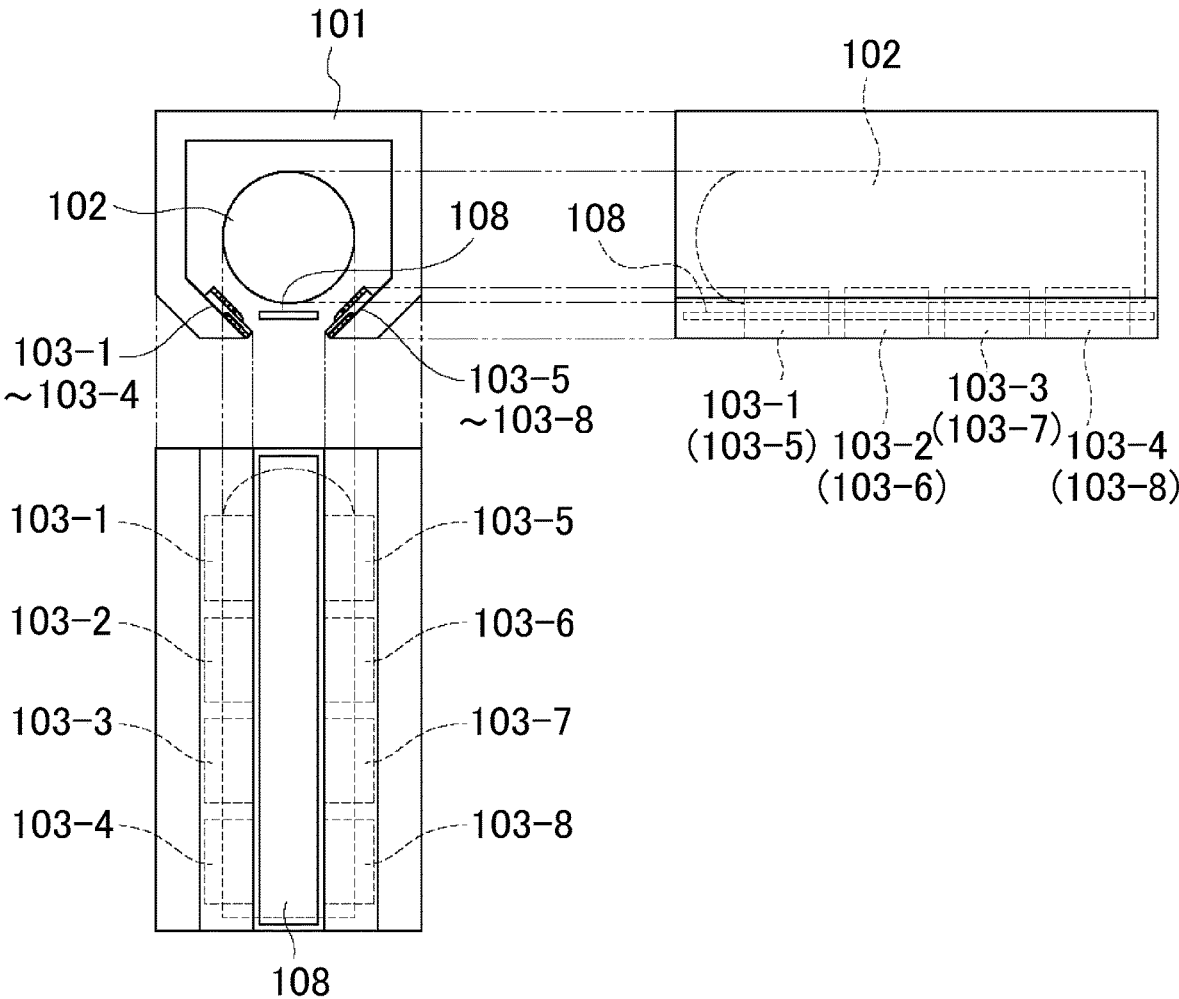
FIG. 2B is a projection view of the active oxygen supply apparatus 101 of the Embodiment 1.
Figure 3:
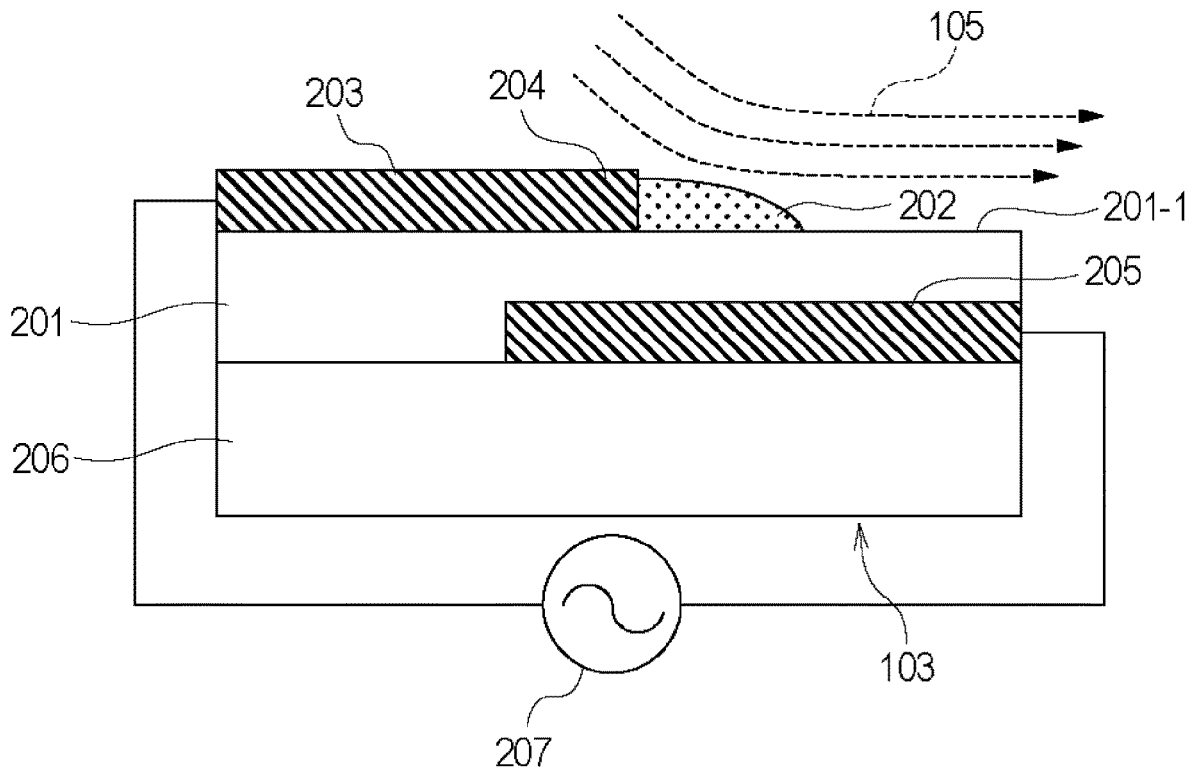
FIG. 3 is a view illustrating an example of a configuration of a plasma generating device 103.
Figure 4:
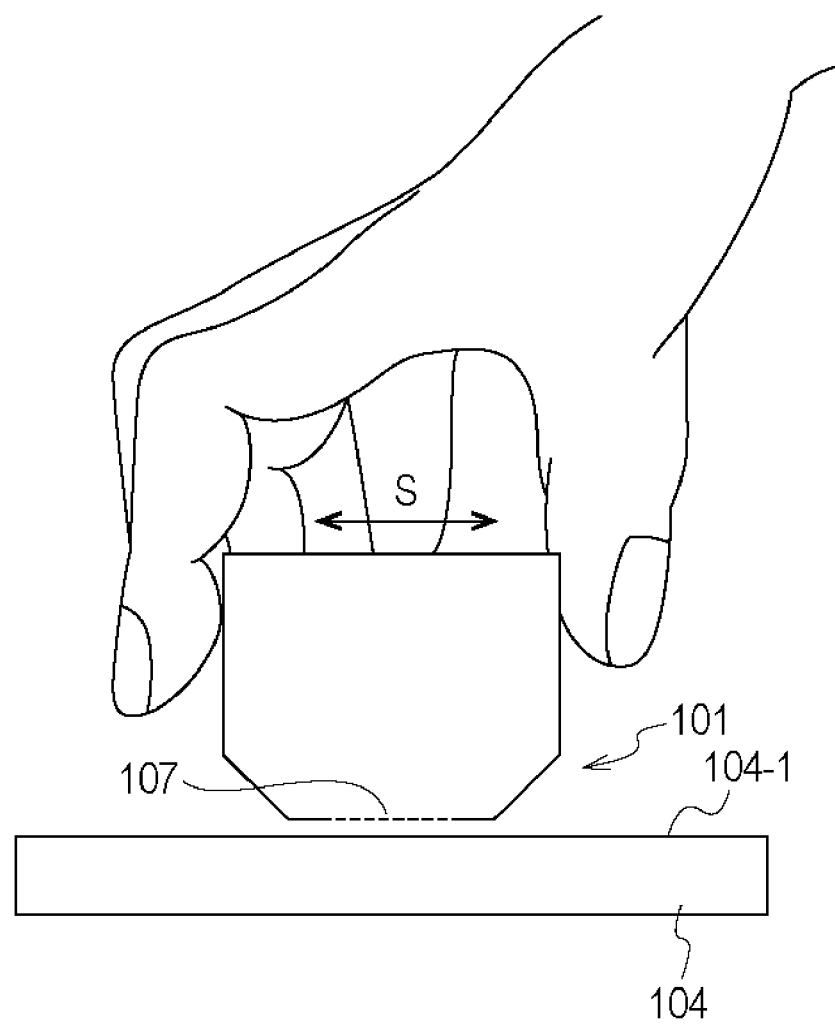
FIG. 4 is a view illustrating an example of a use case of the active oxygen supply apparatus 101 of the Embodiment 1.
Figure 5:
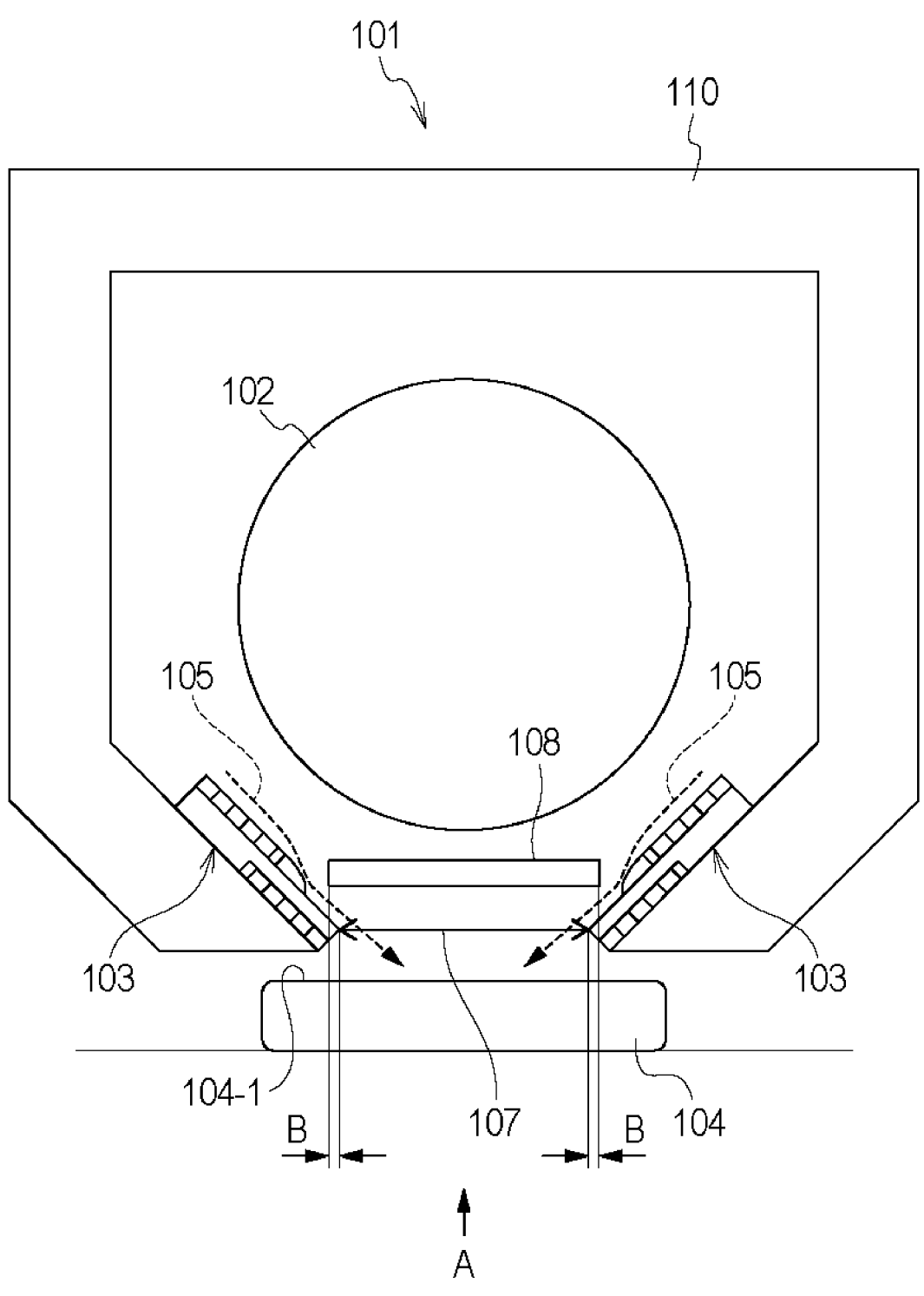
FIG. 5 is a cross-sectional view of a variation of the active oxygen supply apparatus 101 of the Embodiment 1.

From FIG. 1 to FIG. 5 illustrate a configuration of an active oxygen supply apparatus 101 of an Embodiment 1 of the present invention. FIG. 1 is a cross-sectional view of the active oxygen supply apparatus 101. FIG. 2A is a perspective view of the active oxygen supply apparatus 101, and FIG. 2B is a projection view of the active oxygen supply apparatus 101. FIG. 3 is a view illustrating an example of a configuration of a plasma generating device 103. FIG. 4 is a view illustrating an example of a use case of the active oxygen supply apparatus 101. FIG. 5 is a view illustrating a variation of the active oxygen supply apparatus 101 of the Embodiment 1.

Overall Configuration

As shown in FIG. 1 and FIG. 2, the active oxygen supply apparatus 101 in the Embodiment 1 is constituted of a casing 110, an ultraviolet light source 102, the plasma generating device 103, and a shielding plate 108 disposed inside the casing 110, and a power circuit, a base, etc., which are not shown. In addition, the active oxygen supply apparatus 101 in the Embodiment 1 is a cylindrical device that includes a longitudinal direction and a widthwise direction.

The casing 110 has an opening portion 107, as shown in FIG. 1 and FIG. 2. The opening portion 107 includes a longitudinal direction and a widthwise direction, as shown in FIG. 2. In the Embodiment 1, a shape of the opening portion 107 may be rectangular, for example.

In addition, the casing 110 has a first surface and a second surface that are perpendicular to an opening surface of the opening portion 107 and that face each other in a direction parallel to the opening surface of the opening portion 107, as shown in FIG. 2. In this case, the casing 110 has a portion where a distance between the first surface and the second surface in the direction parallel to the opening surface of the opening portion 107 and perpendicular to an axial direction of the ultraviolet light source 102 is equal to or less than 12 cm. In this case, the first surface and the second surface function as a gripped portion to be gripped by a user. Incidentally, the distance is set equal to or less than 12 cm in this case in order to make it a length that is easily gripped by the user. Furthermore, in the Embodiment 1, the first surface and the second surface are described as planar as shown in FIG. 2, but shapes of the first surface and the second surface need not necessarily be planar. For example, the first surface and the second surface may be curved surfaces or convex-concave surfaces. In addition, a material of regions of the first surface and the second surface that are gripped by the user may be different from a material forming the casing 110, for example, a material such as rubber may be used.

The casing 110 includes a connecting surface, as shown in FIG. 1, that connects the first surface and the second surface and that faces the opening surface of the opening portion 107. In the Embodiment 1, the connecting surface is described as planar as shown in FIG. 1, but a shape of the connecting surface need not necessarily be planar. For example, the connecting surface may be a curved surface or a convex-concave surface.

Incidentally, in the Embodiment 1, the active oxygen supply apparatus 101 sanitizes a processed object 104.

The plurality of plasma generating devices 103 (also referred to as plasma actuators) of the Embodiment 1 are aligned parallel to the ultraviolet light source 102, as shown in FIGS. 2A and 2B. In addition, the plasma generating devices 103 are disposed along the opening portion 107 and at both ends of the opening portion in the inside of the casing 110. In the Embodiment 1, plasma generating devices 103-1 to 103-4 are disposed along one edge portion of the opening portion 107 of the casing 110, and plasma generating devices 103-5 to 103-8 are disposed along the other edge portion opposed across the opening portion 107 of the casing 110. In this case, the plasma generating device 103 along the one edge portion of the opening portion 107 of the casing 110 is also referred to as a first plasma generating device, and the plasma generating device 103 along the other edge portion of the opening portion 107 of the casing 110 is also referred to as a second plasma generating device. In addition, an order of arrangement of the first plasma generating device and the second plasma generating device may be reversed.

Furthermore, the one edge portion of the opening portion 107 of the casing 110 is also referred to as an edge portion of a first longitudinal side and the other edge portion of the opening portion 107 of the casing 110 is also referred to as an edge portion of a second longitudinal side. An order of arrangement of the edge portion of the first longitudinal side and the edge portion of the second longitudinal side may be reversed. The plasma generating devices 103-1 to 103-4 are electrically connected in series. Similarly, plasma generating devices 103-5 to 103-8 are electrically connected in series. In addition, the shielding plate 108, which is a separate body from the casing 110, is provided at a position surrounded by the opening portion 107, the ultraviolet light source 102, and the plasma generating device 103. The shielding plate 108 shields an ultraviolet light irradiated by the ultraviolet light source 102. Incidentally, the shielding plate 108 may be integrated to the casing 110.

[Plasma Generating Device]

FIG. 3 is a schematic view illustrating an example of a configuration of the plasma generating device 103. As shown in FIG. 3, the plasma generating device 103 has a first electrode 203 on one surface of a dielectric 201 (hereinafter also referred to as a "first surface") and a second electrode 205 on a surface opposite to the first surface (hereinafter also referred to as a "second surface"). All of the plasma generating devices 103-1 to 103-8 have the same structure.

The plasma generating devices 103-1 to 103-8 have sheet-like structures. The first electrode 203 and the second electrode 205 are disposed diagonally deviated across the dielectric 201 and disposed as being overlapped on a dielectric substrate 206. A power supply 207 applies voltage to the first electrode 203 and the second electrode 205 to generate a plasma 202 from the first electrode 203 toward the second electrode 205. When the plasma 202 is generated from the first electrode 203 toward the second electrode 205, a jet-like flow by the plasma 202 is induced from a corner portion 204 of the first electrode 203 along an exposed portion (a portion not covered by the first electrode 203) 201-1 of the first surface of the dielectric 201. At the same time, a suction flow of air is generated, where the air in the space is directed toward the electrodes. Electrons in the plasma 202 collide with oxygen molecules in the air dissociate the oxygen molecules and generate oxygen atoms. The generated oxygen atoms collide with undissociated oxygen molecules and generate an ozone. Therefore, an induced flow 105 containing a high concentration of the ozone is produced from the corner portion 204 of the first electrode 203 along the surface of the dielectric 201 because of an action between the jet-like flow and the suction flow of air caused by the plasma 202.

In addition, the shorter the shortest distance between the first electrode 203 and the second electrode 205 is, the easier it is for the plasma generating device 103 to generate the plasma. Therefore, the thinner a film thickness of the dielectric 201 is, the more preferable it is as long as it does not cause an electrical insulation breakdown, and the film thickness may be from 10 μm to 1000 μm, preferably from 10 μm to 200 μm. In addition, it is preferable for the shortest distance between the first electrode 203 and the second electrode 205 to be equal to or less than 200 μm.

Incidentally, in the Embodiment 1, the plasma generating device 103 is disposed along the edge portion of the opening portion 107 so that the induced flow 105 containing the high concentration of the ozone induced by the plasma generating device 103 flows toward the opening portion 107. Incidentally, a location where the plasma generating device 103 is disposed need not necessarily be along the edge portion of the opening portion 107. The arrangement is not limited to the configuration above as long as the plasma generating device 103 is disposed in the inside of the casing 110 and on a surface where the edge portion of the opening portion 107 exists, and the induced flow 105 flows toward the opening portion 107.

[Ultraviolet Light Source and Ultraviolet Light]

Next, the ultraviolet light source 102 is described. The ultraviolet light source 102 irradiates the ultraviolet light into the induced flow 105 containing the ozone generated by the plasma generating device 103. When the induced flow 105 containing the ozone is irradiated by the ultraviolet light source 102, the ozone contained in the induced flow 105 is excited and the active oxygen is generated. Since a peak value of an optical absorption spectrum of the ozone is 260 nm, a peak wavelength of the ultraviolet light irradiated by the ultraviolet light source 102 is preferable to be from 220 nm to 310 nm. Furthermore, in order to efficiently generate the active oxygen, it is more preferable for the peak wavelength of the ultraviolet light of the ultraviolet light source 102 to be from 253 nm to 285 nm, and even more preferable to be from 253 nm to 266 nm.

A specific ultraviolet light source used for the ultraviolet light source 102 includes a low-pressure mercury lamp in which mercury is enclosed in quartz glass along with an inert gas such as argon or neon, a cold cathode tube ultraviolet light lamp (UV-CCL), an ultraviolet LEDs, etc. A wavelength of the low-pressure mercury lamp and the cold cathode tube ultraviolet light lamps may be selected from 254 nm, etc. On the other hand, a wavelength of the ultraviolet LEDs may be selected from 265 nm, 275 nm, 280 nm, etc. in terms of output performance. Incidentally, the ultraviolet light source 102 in the Embodiment 1 is not limited to the configuration above as long as it can irradiate the ultraviolet light that is capable of generating the active oxygen.

[Arrangement of Plasma Generating Device 103, Ultraviolet Light Source 102 and Processed Object 104]

Next, an arrangement of the plasma generating device 103, the ultraviolet light source 102, and the processed object 104 in the active oxygen supply apparatus 101 is described. The plasma generating device 103, which generates the induced flow 105 containing the ozone in the active oxygen supply apparatus 101, is disposed along the edge portion of the opening portion 107 of the casing 110 so that the induced flow 105 flows toward the opening portion 107, as described above. In addition, it is not limited to the arrangement above as long as the active oxygen generated in the induced flow 105 is supplied from the opening portion 107 to the processed object 104 before the active oxygen is decomposed.

Furthermore, in FIG. 3, the plasma generating device 103 is disposed so that an extension line along a direction from the corner portion 204 of the first electrode of the plasma generating device 103 to the exposed portion 201-1 of the first surface of the dielectric is to be a predetermined angle to a processed surface 104-1 of the processed object 104. That is, the plasma generating device 103 is disposed so that a dotted arrow shown in FIG. 1 as the induced flow 105 is to be the predetermined angle to the processed surface 104-1 of the processed object 104. In this case, it is preferable for the predetermined angle to be from 0° to 90°, and even more preferable to be from 0° to 45°.

By being disposed as described above, the active oxygen generated by the irradiation of the ultraviolet light to the induced flow 105 containing the ozone by the ultraviolet light source 102 is supplied to the processed object 104 through the opening portion 107. In addition, the induced flow 105 containing active oxygen, having a certain degree of flow velocity, can be supplied locally to the processed surface 104-1 of the processed object 104.

[Action]

The active oxygen supply apparatus 101 in the Embodiment 1 irradiates the ultraviolet light to the induced flow 105 containing the ozone by the ultraviolet light source 102 to generate the active oxygen in the induced flow 105. The active oxygen generated in the induced flow 105 can then be supplied to the processed surface 104-1 of the processed object 104, or, for example, to a spatial region from the processed surface 104-1 to a height of about 1 mm. Therefore, the active oxygen can be supplied to the processed surface 104-1 of the processed object 104 before the generated active oxygen is decomposed into oxygen and water. As a result, the processed surface 104-1 of the processed object 104 is sterilized by the active oxygen.

Next, an example of a use case of the active oxygen supply apparatus 101 in the Embodiment 1 is described.

In FIG. 4, the opening portion 107 is placed over the processed object 104 so that the opening portion 107 faces downward. As shown in FIG. 4, the user grips the first surface and the second surface as described above of the active oxygen supply apparatus 101. The user directs the opening portion 107 (indicated by a dashed line) of the active oxygen supply apparatus 101 toward the processed surface 104-1 of the processed object 104 and drives the active oxygen supply apparatus 101 in a state where the opening portion 107 and the processed surface 104-1 are parallel to each other. When an area of the processed surface 104-1 is larger than an area of the opening portion 107, the user moves the active oxygen supply apparatus 101 along the processed surface 104-1 in a direction of the arrow S so that the opening portion 107 scans the processed surface 104-1. By moving the active oxygen supply apparatus 101 in this manner, the user can sanitize the entire processed surface 104-1.

In addition, the shielding plate 108 is disposed in the active oxygen supply apparatus 101 of the Embodiment 1 as shown in FIG. 1. The shielding plate 108 is disposed between the opening portion 107 of the casing 110 and the ultraviolet light source 102, and shields the ultraviolet light irradiated from the opening portion 107 of the casing 110 to the outside of the casing 110. Incidentally, the shielding plate 108 is disposed so that a distance between the shielding plate 108 and the processed object 104 is longer than a distance between the plasma generating device 103 and the processed object 104.

By providing a shielding plate 108 in this manner, it is possible to keep the user from viewing directly the ultraviolet light irradiated by the ultraviolet light source 102 and to keep the user's skin from being exposed to the ultraviolet light when the user uses the active oxygen supply apparatus 101. Incidentally, the shielding plate 108 may be disposed so that a portion of the shielding plate 108 (indicated by arrows B) overlaps the casing 110 forming the opening portion 107 when the opening surface of the opening portion 107 is viewed from a direction perpendicular to the opening surface (a direction of an arrow A), as shown in FIG. 5. By disposing the shielding plate 108 in this manner, a risk for the user to be exposed to the ultraviolet light can be further reduced. In addition, by disposing the shielding plate 108, the active oxygen generated in the induced flow 105 flows between the plasma generating device 103 and the shielding plate 108 by the induced flow 105 and is supplied to the processed object 104. Therefore, it is possible to keep the active oxygen generated in the induced flow 105 from remaining in the casing 110, and the active oxygen can be efficiently supplied to the processed surface 104-1.

Embodiment 2

Figure 6:
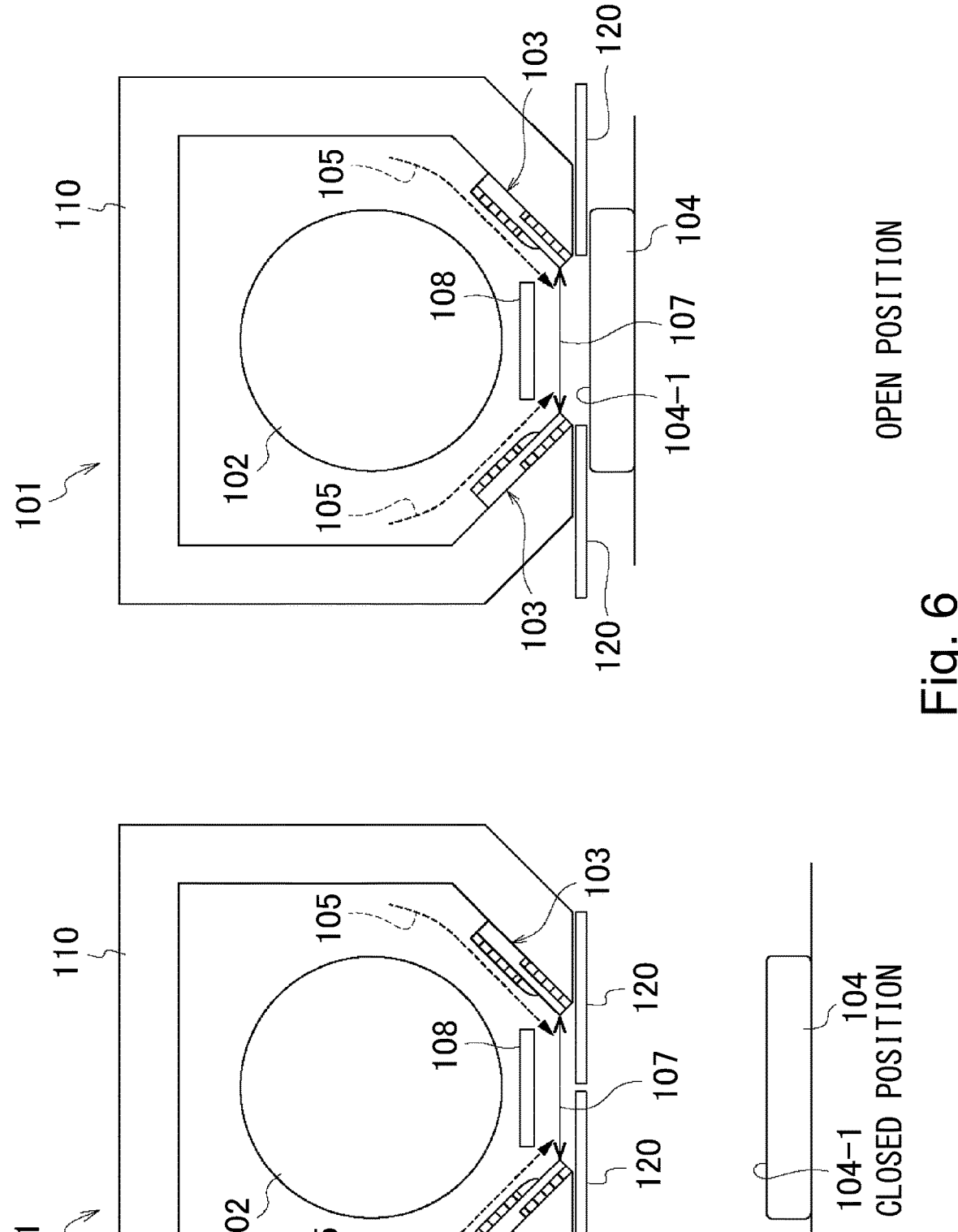
FIG. 6 is a cross-sectional view illustrating an example of a configuration with a shutter 120 provided in an active oxygen supply apparatus 101 of an Embodiment 2.

Next, a configuration of an Embodiment 2 is described with referring to FIG. 6. FIG. 6 illustrates an example of a configuration of the active oxygen supply apparatus 101 of the Embodiment 2, in which a shutter 120 is provided. The shutter 120 is disposed in the casing 110 and switches between a closed position and an opened position. When the shutter 120 is in the closed position, the opening portion 107 is in a closed state, and when the shutter 120 is in the open position, the opening portion 107 is in an exposed state. In addition, the shutter 120 is urged to be in the closed position by an urging member not shown.

In the Embodiment 2, when the user uses the active oxygen supply apparatus 101, the shutter 120 is held in the opened position. After the user uses the active oxygen supply apparatus 101, the shutter 120, which was held in the opened position, returns to the closed position. By returning the shutter 120 to the closed position after use, it is possible to keep the active oxygen and the ozone generated in the active oxygen supply apparatus 101 from flowing out of the apparatus. As a result, it is possible to keep the user from being exposed to the active oxygen and the ozone. Incidentally, the shutter 120 can be opened and closed by a switch not shown being pressed by the user.

In addition, the opening and the closing of the shutter 120 can be interrelated with ON/OFF of a switch that drives the active oxygen supply apparatus 101. In this case, when the shutter 120 is in the opened position, the switch is turned ON and the active oxygen supply apparatus 101 is driven. When the shutter 120 is in the closed position, the switch is turned OFF and the active oxygen supply apparatus 101 is stopped. In addition, a timer may be provided in the active oxygen supply apparatus 101, and when a predetermined time elapses after the shutter 120 is in the opened position and the switch turns ON, the shutter 120 may come to be in the closed position and the switch may turn OFF.

By controlling in this manner, it is possible to improve operability and to keep the user from being exposed to the active oxygen, the ultraviolet light, and the ozone.

Embodiment 3

Figure 7:
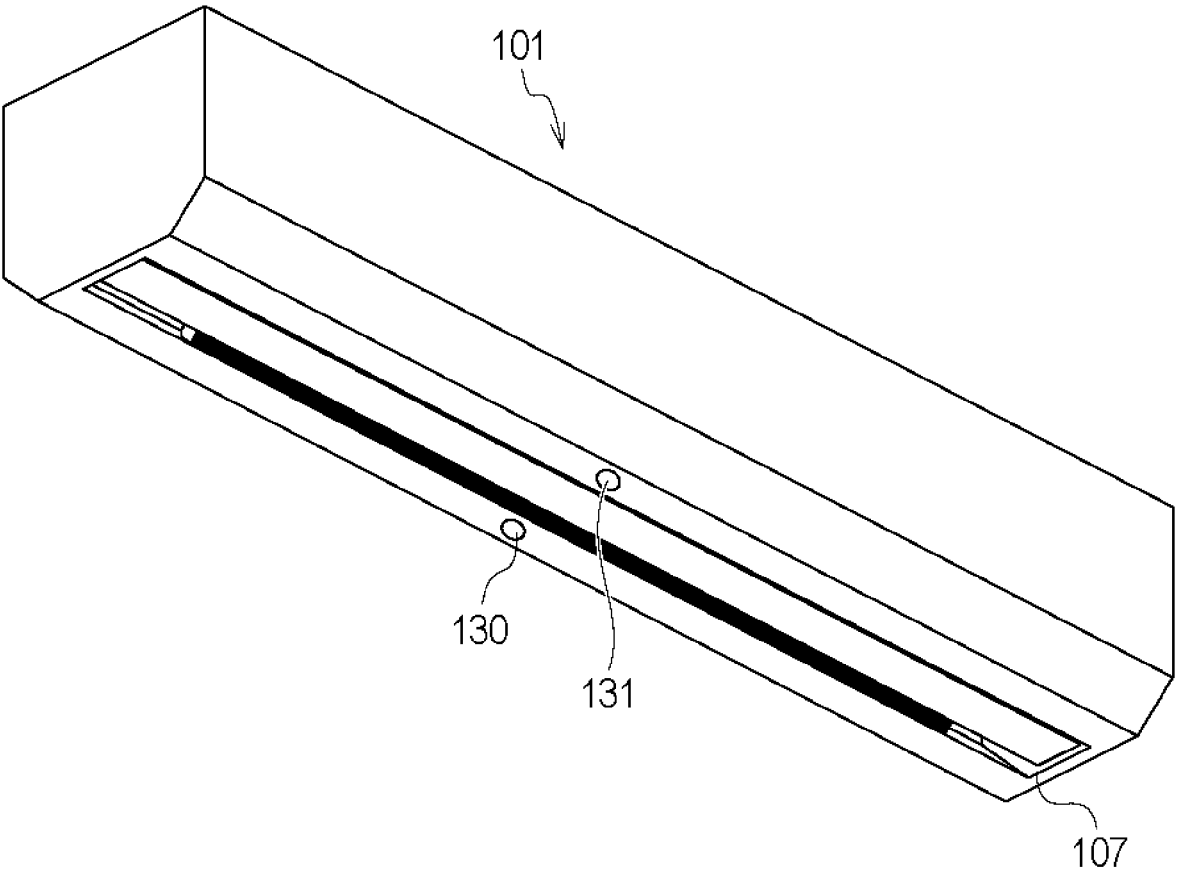
FIG. 7 is a perspective view illustrating an example of a configuration with a proximity sensor 130 and a human detecting sensor 131 provided in a vicinity of an opening portion 107 in an active oxygen supply apparatus 101 of an Embodiment 3.

Next, a configuration of an Embodiment 3 is described with referring to FIG. 7. FIG. 7 illustrates an example of a configuration of the active oxygen supply apparatus 101 of the Embodiment 3, in which a proximity sensor 130 and a human detecting sensor 131 are provided in a vicinity of the opening portion 107. Incidentally, the proximity sensor 130 is also referred to as a proximity detection means, and the human detecting sensor 131 is also referred to as a human body detection means. The proximity sensor 130 detects a distance between the active oxygen supply apparatus 101 and the processed object 104. Then, the active oxygen supply apparatus 101 turns on a switch of the active oxygen supply apparatus 101 when the distance to the processed object 104 is less than a predetermined distance according to a detection result by the proximity sensor 130. In this case, when a person approaches as a processed object 104, there is a risk that a skin of the parson may be exposed to the active oxygen. In consideration of such a case, the human detecting sensor 131 detects a distance between the active oxygen supply apparatus 101 and a human body. And the active oxygen supply apparatus 101 turns on the switch of the active oxygen supply apparatus 101 when the distance to the human body is greater than a predetermined distance according to a detection result by the human detecting sensor 131. As a result, the active oxygen generated by the active oxygen supply apparatus 101 can be surely supplied to the processed surface 104-1 of the processed object 104 to be sterilized. In addition, it is possible to keep a human from being exposed to the active oxygen.

Embodiment 4

Figure 8:
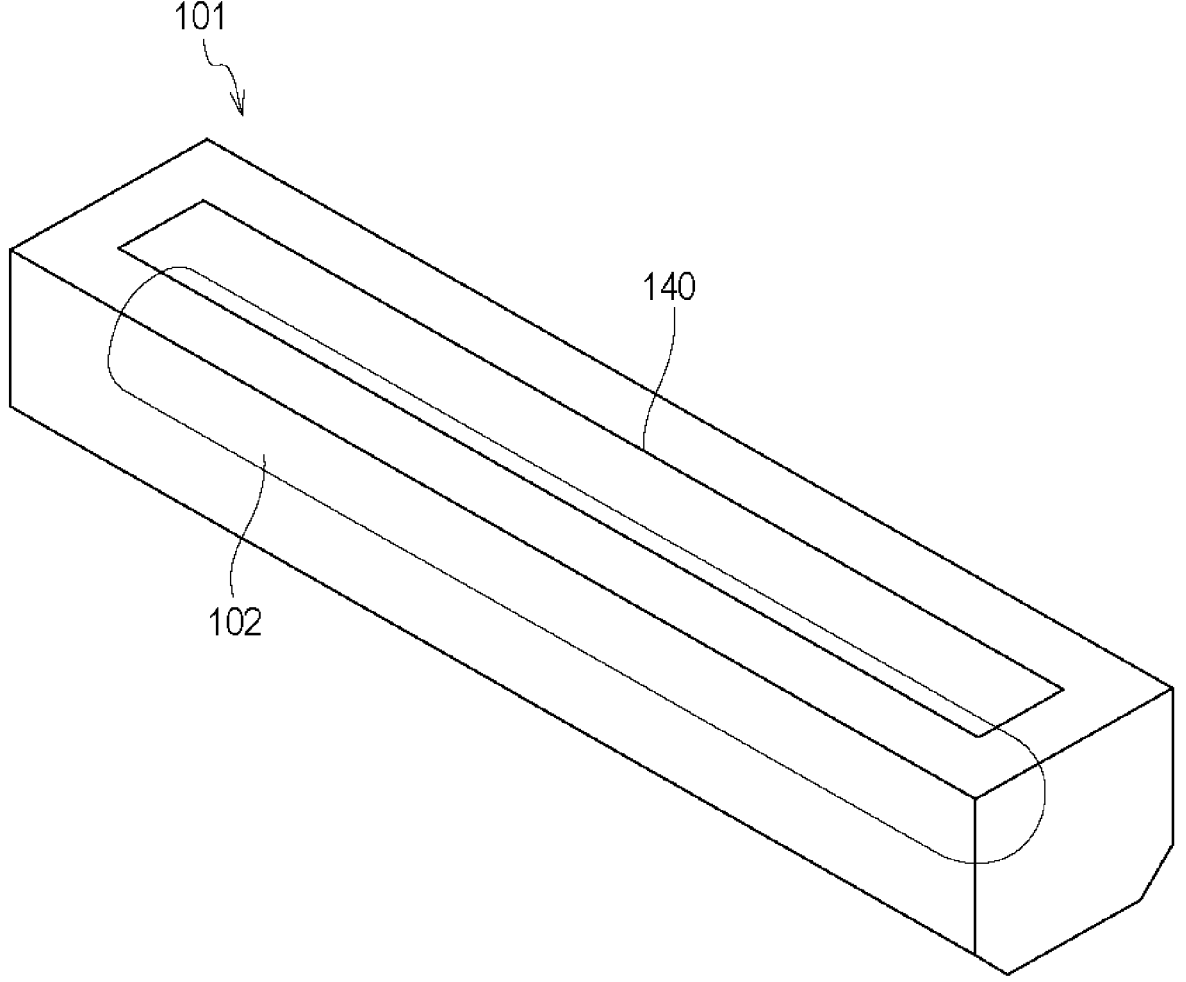
FIG. 8 is a perspective view illustrating an example of a configuration with a transparent window portion 140 provided in a part of a casing 110 in an active oxygen supply apparatus 101 of an Embodiment 4.

Next, a configuration of an Embodiment 4 is described with referring to FIG. 8. FIG. 8 illustrates an example of a configuration of the active oxygen supply apparatus 101 of the Embodiment 4, in which a transparent window portion 140 is provided in a part of the casing 110.

By providing the window portion 140 made of a material that blocks the ultraviolet light in the part of the casing 110, it becomes possible for the user to see the ultraviolet light source 102 is irradiating the ultraviolet light and can confirm that the active oxygen supply apparatus 101 is working. The window portion 140 need not be transparent in color and may be made of translucent or light-colored material. As a result, it is possible to ensure visibility while keeping the user from being exposed to the ultraviolet light. Incidentally, a notification means may be provided in the casing 101 to notify that the ultraviolet light is irradiated by the ultraviolet light source 102.

Embodiment 5

Figure 9:
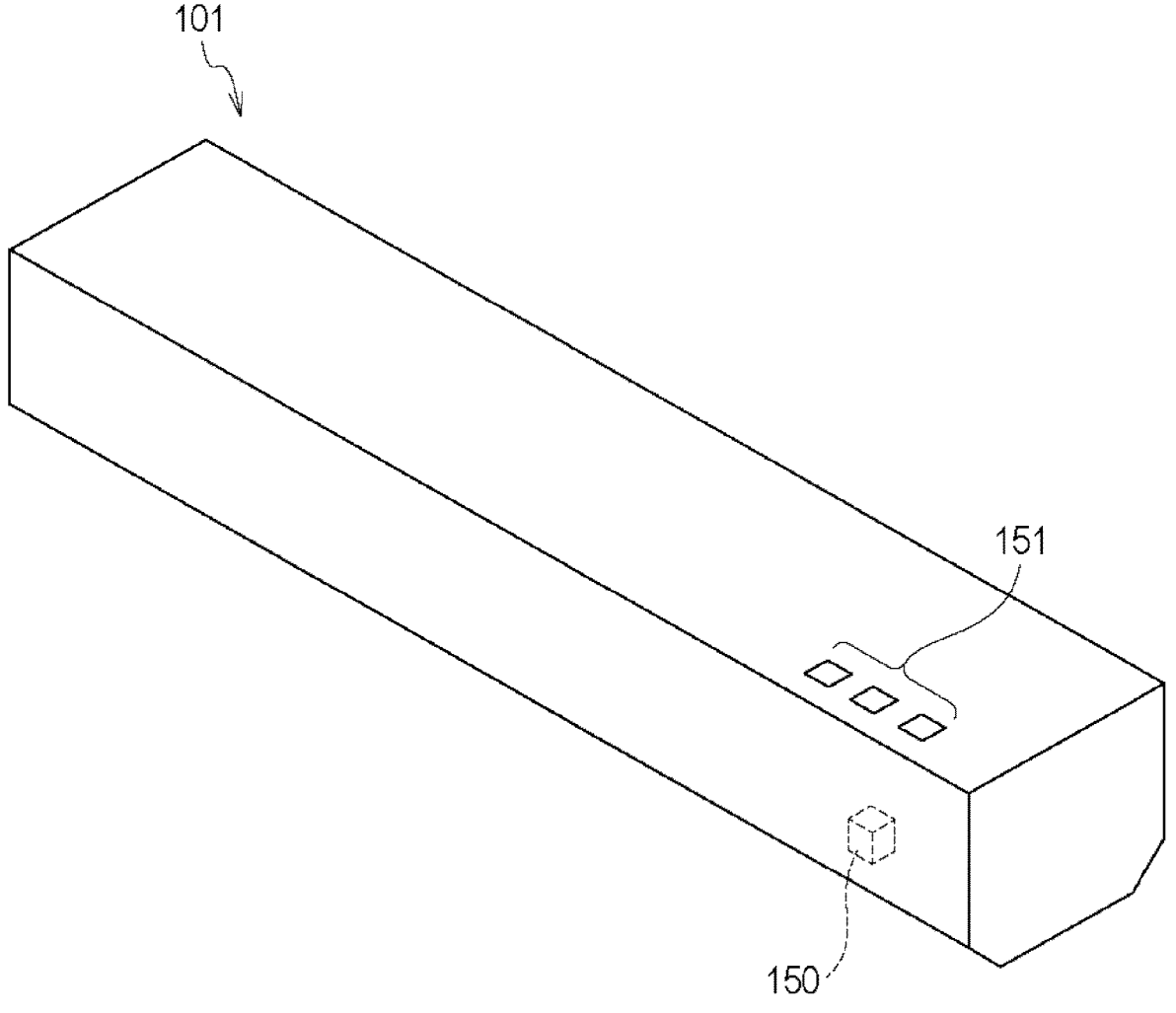
FIG. 9 is a perspective view illustrating an example of a configuration with an acceleration sensor 150 and an indicator 151 provided in an active oxygen supply apparatus 101 of an Embodiment 5.

Next, a configuration of an Embodiment 5 is described with referring to FIG. 9. FIG. 9 illustrates an example of a configuration of the active oxygen supply apparatus 101 of the Embodiment 5, in which an acceleration sensor 150 and an indicator 151 are provided. Incidentally, the acceleration sensor 150 is also referred to as an acceleration detection means and the indicator 151 is also referred to as a speed notification means. When the active oxygen supply apparatus 101 is moved at a high speed by the user, there is a risk that a predetermined amount or a predetermined concentration of the active oxygen may not be supplied to the processed object 104. In addition, a flow of the induced flow 105 may be affected by an air flow that is generated because of the active oxygen supply apparatus 101 being moved at a high speed by the user. In consideration of such a case, the active oxygen supply apparatus 101 in the Embodiment 5 includes the acceleration sensor 150. The acceleration sensor 150 detects that the active oxygen supply apparatus 101 is moved. The active oxygen supply apparatus 101 determines whether a speed at which the active oxygen supply apparatus 101 is moved is within a predetermined speed range based on a detection value of the acceleration sensor 150 and notifies the user of a determined result by the indicator 151. In this case, for example, when the active oxygen supply apparatus 101 is moved within the predetermined speed range, the indicator 151 is lit. Incidentally, the indicator 151 may be turned on as a warning when the active oxygen supply apparatus 101 is moved outside the predetermined speed range.

This configuration allows the user to operate the active oxygen supply apparatus 101 while visually observing a lighting state of the indicator 151 and adjusting the speed of moving the active oxygen supply apparatus 101. As a result, it is possible to keep a predetermined amount or a predetermined concentration of the active oxygen to the processed object 104 from not being supplied because of the active oxygen supply apparatus 101 being moved at a fast speed. In addition, in the Embodiment 5, it is possible to keep the flow of the induced flow 105 from being affected by the air flow generated by the active oxygen supply apparatus 101 being moved at a fast speed.

Embodiment 6

Figure 10:
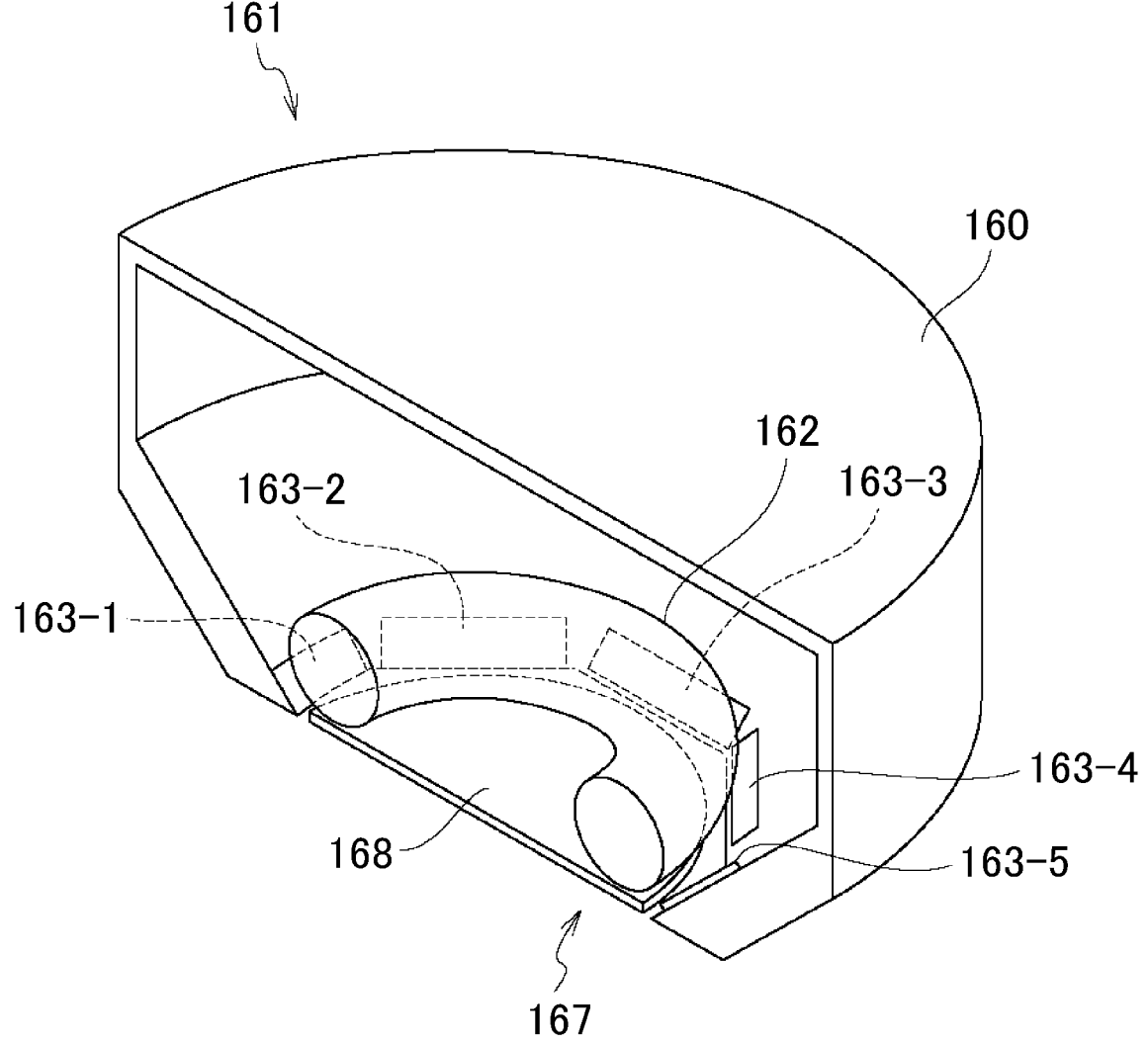
FIG. 10 is a perspective view illustrating an example of a configuration in which a casing 160 is cylindrical in an active oxygen supply apparatus 161 of an Embodiment 6.

Next, a configuration of an Embodiment 6 is described with referring to FIG. 10. FIG. 10 illustrates an example of a configuration of an active oxygen supply apparatus 161 of the Embodiment 6, in which a casing 160 is cylindrical, and illustrates a state being cut at the center. The active oxygen supply apparatus 101 of the Embodiment 1 was a cylindrical device that included the longitudinal direction and the widthwise direction as shown in FIG. 2. In addition, the opening portion 107 of the active oxygen supply apparatus 101 also has the longitudinal direction and the widthwise direction, and a range of sterilization is different between a case where the user moves the active oxygen supply apparatus 101 in the longitudinal direction and a case where the user moves the active oxygen supply apparatus 101 in the widthwise direction. In consideration of such cases where the range that can be sterilized differs depending on the direction in which the device is moved, the casing 160 is cylindrical in the Embodiment 6. Plasma generating devices 163 (163-1 to 163-5 in FIG. 10) are disposed radially around an opening portion 167 so that they are opposed across the circular opening portion 167. In addition, a shielding plate 168 is disposed between the opening portion 167 and an ultraviolet light source 162. According to the configuration of the Embodiment 6, the same sterilization effect as of Example 1 can be obtained no matter in which direction an apparatus is moved.

Embodiment 7

Figure 11:
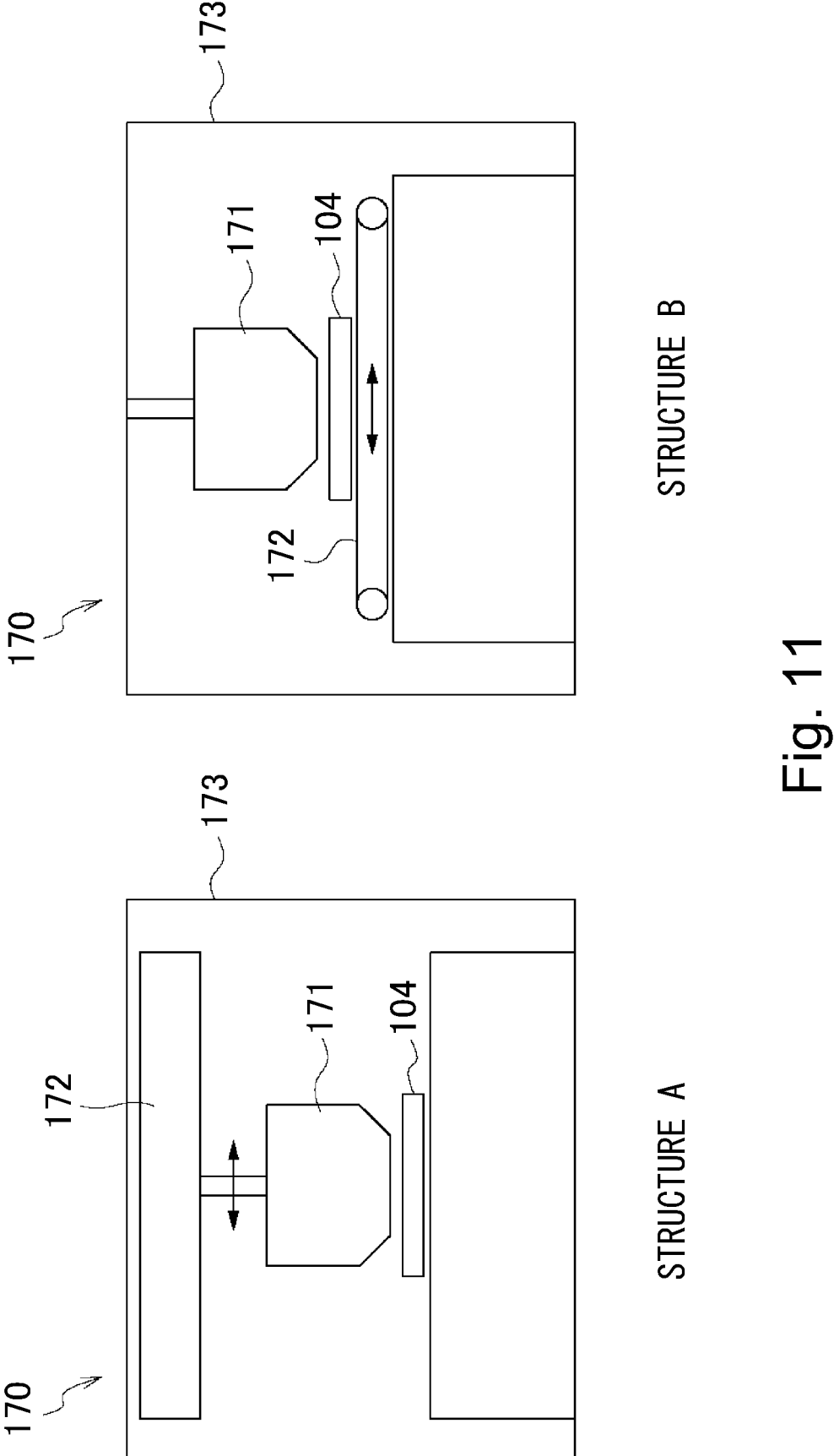
FIG. 11 is a cross-sectional view illustrating an example of a configuration with an active oxygen supply apparatus 171 and a moving means 172 for moving a position of the active oxygen supply apparatus 171 relative to a processed object 104 in a processing apparatus 170 of an Embodiment 7.

Next, a configuration of an Embodiment 7 is described with referring to FIG. 11. FIG. 11 illustrates an example of an embodiment of a processing apparatus 170, which is constituted of an active oxygen supply apparatus 171 and a moving means 172 for moving a position of the active oxygen supply apparatus 171 relative to the processed object 104. Incidentally, the processing apparatus 170 is also referred to as an active oxygen supply apparatus. The moving means 172 may be configured to move the active oxygen supply apparatus 171 with respect to the processed object 104 as shown in FIG. 11 (configuration A). The moving means 172 in this case is also referred to as a first moving means. The moving means 172 may be configured to move the processed object 104 with respect to the active oxygen supply apparatus 171 as shown in FIG. 11 (configuration B). The moving means 172 in this case is also referred to as a second moving means. According to the Embodiment 7, by placing the processed object 104 at a predetermined position in the processing apparatus 170, the active oxygen supply apparatus 171 or the processed object 104 is moved and a sterilization process is automatically performed. This reduces a burden on the user to move the active oxygen supply apparatus 171. In addition, by moving the active oxygen supply apparatus 171 at an optimal speed, the user can reliably obtain a treatment effect. Incidentally, in the Embodiment 7, as shown in FIG. 11, it is configured that a casing 173 covers the active oxygen supply apparatus 171 and the moving means 172. By disposing the casing 173, it is possible to keep a user from being exposed to an ultraviolet light. For this reason, the shielding plate 108 described in Embodiment 1 need not be provided.

Incidentally, usages of the active oxygen supply apparatus 101 in the above embodiments are not limited to sterilization of the processed object 104. For example, by supplying the active oxygen to the processed object 104, deodorization of the processed object 104, bleaching of the processed object 104, hydrophilic surface treatment of the processed object 104, etc. can also be performed.

INDUSTRIAL APPLICABILITY

According to the present invention, an active oxygen supply apparatus capable of supplying active oxygen is provided.

The present invention is not limited to the above embodiments, and various changes and variations are possible without departing from the spirit and scope of the present invention. Therefore, the following claims are attached to publicly disclose the scope of the present invention.

The invention claimed is:

1. An active oxygen supply apparatus comprising:

a casing;

a plurality of plasma generating devices provided in an inside of the casing and configured to generate an induced flow containing ozone;

an ultraviolet light source provided in the inside of the casing and configured to irradiate the induced flow containing the ozone with ultraviolet light;

a shielding plate provided in the inside of the casing and configured to shield the ultraviolet light irradiated from passing to an outside of the casing through an opening portion of the casing; and a shutter configured to be switched between a closed position and an opened position, wherein an active oxygen generated by irradiating the induced flow containing the ozone with the ultraviolet light from the ultraviolet light source is supplied to the outside of the casing through the opening portion of the casing, and wherein the opening portion becomes a closed state when the shutter is in the closed position and the opening portion becomes an exposed state when the shutter is in the opened position.

2. The active oxygen supply apparatus according to claim 1, wherein the induced flow flows toward the opening portion of the casing.

3. The active oxygen supply apparatus according to claim 1, wherein the plurality of plasma generating devices are disposed on a surface where an edge portion of the opening portion exists in the inside of the casing.

4. The active oxygen supply apparatus according to claim 3, wherein when an opening surface of the opening portion of the casing is seen in a direction perpendicular to the opening surface, at least a part of the shielding plate is disposed so as to overlap with the casing which forms the opening portion.

5. The active oxygen supply apparatus according to claim 1, wherein a distance between the shielding plate and a processed object is longer than a distance between the plasma generating devices and the processed object.

6. The active oxygen supply apparatus according to claim 1, wherein the plurality of plasma generating devices are disposed along an edge portion of the opening portion of the inside of the casing and opposed across the opening portion.

7. The active oxygen supply apparatus according to claim 1, wherein the casing includes a first surface and a second surface in a direction perpendicular to an opening surface of the opening portion of the casing, the first surface and the second surface being opposed each other with respect to a direction parallel to the opening surface of the opening portion of the casing.

8. The active oxygen supply apparatus according to claim 7, wherein a distance between the first surface and the second surface with respect to the direction parallel to the opening surface of the opening portion of the casing is equal to 12 cm or less.

9. The active oxygen supply apparatus according to claim 1, wherein a shape of the opening portion of the casing is a rectangle, and wherein the plurality of the plasma generating devices include a first plasma generating device and a second plasma generating device, the first plasma generating device is disposed along an edge portion of a first longitudinal side of the opening portion of the casing and the second plasma generating device is disposed along an edge portion of a second longitudinal side of the opening portion of the casing, and the first plasma generating device and the second plasma generating device are opposed across the opening portion.

10. The active oxygen supply apparatus according to claim 1, wherein a shape of the opening portion of the casing is a circle, and wherein the plurality of the plasma generating devices include a first plasma generating device and a second plasma generating device, and the first plasma generating device and the second plasma generating device are disposed along an edge portion of the opening portion.

11. The active oxygen supply apparatus according to claim 1, wherein the plurality of the plasma generating devices are driven when the shutter is in the opened position.

12. The active oxygen supply apparatus according to claim 11, wherein by elapsing a predetermined period after the shutter is in the opened position and the plurality of the plasma generating devices are driven, the shutter is in the closed position and the plurality of the plasma generating devices are stopped.

13. The active oxygen supply apparatus according to claim 1, further comprising a proximity detection means configured to detect a distance between the opening portion and a processed object to which the active oxygen is supplied in the outside of the casing, wherein the proximity detection means causes to drive the plurality of the plasma generating devices when a distance between the opening portion and a processed object becomes shorter than a predetermined distance.

14. The active oxygen supply apparatus according to claim 1, further comprising a human body detection means configured to detect a distance between the opening portion and a human body, wherein the human body detection means causes to stop driving of the plurality of the plasma generating devices when a distance between the opening portion and the human body becomes shorter than a predetermined distance.

15. The active oxygen supply apparatus according to claim 1, further comprising a window portion made of a material that blocks the ultraviolet light, and through which a working state of the ultraviolet light source can be seen.

16. The active oxygen supply apparatus according to claim 1, further comprising a notification means configured to notify that the ultraviolet light is irradiated by the ultraviolet light source in the casing.

17. The active oxygen supply apparatus according to claim 1, further comprising:

an acceleration detection means configured to detect an acceleration of the active oxygen supply apparatus; and a speed notification means configured to determine whether the active oxygen supply apparatus is moved within a predetermined speed according to a detection result of the acceleration detection means and notify a determined result.

18. An active oxygen supply processing apparatus comprising:

a first moving means configured to move the active oxygen supply apparatus according to claim 1, wherein the first moving means causes the active oxygen supply apparatus to move along a surface of a processed object in a state in which the opening portion and the surface of the processed object to which the active oxygen is supplied in the outside of the casing are parallel, and supplies the active oxygen to the surface of the processed object.

19. An active oxygen supply processing apparatus comprising:

a second moving means configured to move a position of a processed object to which the active oxygen is supplied relative to the active oxygen supply apparatus according to claim 1, wherein the second moving means causes the processed object to move along the opening portion of the oxygen supply processing apparatus in a state in which the opening portion and a surface of the processed object are parallel, and supplies the active oxygen to the surface of the processed object.

\* \* \* \* \*